United States Patent [19]
Benzinger

[11] Patent Number: 6,006,760
[45] Date of Patent: *Dec. 28, 1999

[54] SHAVING KIT

[76] Inventor: Robert W. Benzinger, 3461 Rockaway Ave., Annapolis, Md. 21403

[ * ] Notice: This patent is subject to a terminal disclaimer.

[21] Appl. No.: 08/471,457

[22] Filed: Jun. 6, 1995

Related U.S. Application Data

[63] Continuation-in-part of application No. 08/417,890, Apr. 6, 1995, abandoned.

[51] Int. Cl.$^6$ ................................................. A45D 40/00
[52] U.S. Cl. .......................... 132/286; 132/292; 132/289; 30/41; 206/208
[58] Field of Search ................... 132/200, 292, 132/286, 249, 289; 30/41, 34.2; 206/208; 222/192, 129, 321.1, 321.7

[56] References Cited

U.S. PATENT DOCUMENTS

| | | | |
|---|---|---|---|
| 788,437 | 9/1904 | Slevin | 30/41 |
| 1,189,118 | 6/1916 | Jonas | 30/41 |
| 1,654,379 | 12/1927 | Matzka | 222/192 |
| 1,912,627 | 6/1933 | Dyer | 206/208 |
| 1,981,853 | 11/1934 | Bruce | 206/16 |
| 2,027,899 | 1/1936 | Bruce | 206/16 |
| 2,177,815 | 10/1939 | Strock | 21/105 |
| 2,349,183 | 5/1944 | Mahler | 21/87 |
| 3,063,907 | 11/1962 | Sharawara | 167/85 |
| 3,352,630 | 11/1967 | Fischer et al. | 21/90 |
| 3,477,127 | 11/1969 | Regan | 30/41 |
| 3,599,684 | 8/1971 | Elias | 141/369 |
| 3,777,597 | 12/1973 | Herb | 83/22 |
| 3,808,920 | 5/1974 | Fisher | 83/22 |
| 3,949,067 | 4/1976 | Gibbs | 424/73 |
| 4,101,339 | 7/1978 | Kaneko et al. | 134/2 |
| 4,170,821 | 10/1979 | Booth | 30/41 |
| 4,384,589 | 5/1983 | Morris | 40/30 |
| 4,618,433 | 10/1986 | Allison, III | 252/8.514 |
| 4,733,467 | 3/1988 | Borenstein | 30/41 |
| 4,741,915 | 5/1988 | Farr et al. | 426/542 |
| 4,963,350 | 10/1990 | Goldstein et al. | 424/73 |
| 5,095,619 | 3/1992 | Davis et al. | 30/41 |
| 5,319,852 | 6/1994 | Metzger | 30/90 |
| 5,345,680 | 9/1994 | Vreeland et al. | 19/40 |

FOREIGN PATENT DOCUMENTS

| | | | |
|---|---|---|---|
| 2551391 | 3/1985 | France | 26/21 |
| 805544 | 5/1951 | Germany . | |
| 162854 | 10/1933 | Switzerland . | |

OTHER PUBLICATIONS

Product Alert, Oct. 24, 1994 (Form Dialog).

*Primary Examiner*—Gene Mancene
*Assistant Examiner*—Philogene Pedro
*Attorney, Agent, or Firm*—Millen, White, Zelano & Branigan

[57] ABSTRACT

A system for and method of shaving includes a bath of an evaporative astringent material such as witch hazel extract and alcohol in which a razor head is soaked after each shave and is used for the next shave while still wet with the material of the bath.

15 Claims, 4 Drawing Sheets

SHAVING KIT

RELATED APPLICATION

The present application is a continuation-in-part of U.S. patent application Ser. No. 08/417,890, filed Apr. 6, 1995 now abandoned and is related to the patent application titled "Shaving Method" filed on even date by the same inventor all of whose disclosures are entirely incorporated by reference herein.

FIELD OF THE INVENTION

The present invention relates to methods and systems for shaving hair from a person's face or body. More particularly, the present invention relates to shaving systems which include a shaving razor or shaver, liquid and optionally shaving lather or gel and to methods of using such systems.

BACKGROUND CONSIDERATIONS

Typically, men shave facial hair once a day and women shave their legs and under arms periodically. This can be an uncomfortable temporarily disfiguring and painful. In addition, razor pull can make shaving unpleasant and time consuming.

Shaving can also be expensive because blades become dull relatively quickly due to corrosion and other factors which result from shavers not thoroughly cleaning their razors as well as from the condition of water used when shaving. In addition, the cutting edges of razor blades tend to corrode when left exposed to the atmosphere after having been subjected to the mechanical stress of cutting hair and the chemical action of tap water and corrosive components in shaving lathers and gels.

SUMMARY OF THE INVENTION

In view of the aforementioned considerations, the present invention is directed to a shaving system and method in which a razor is allowed to soak in liquid after use, preferably after each use, and is then used while wet with the liquid for the subsequent shave.

In a more specific aspect, evaporation cools the liquid and the blade or blades of the razor so that the razor is applied cold to the shaver's skin.

In accordance with a more specific aspect of the invention, the liquid includes an astringent.

In accordance with still a more specific aspect of the invention, the liquid includes witch hazel.

In order to apply the evaporative liquid directly to the patient's face in relatively large quantities, the razor may include a strip of material which retains a quantity of the liquid on the razor adjacent the blade or blades thereof.

In accordance with one embodiment of the invention, the liquid retaining material is sponge material and is positioned behind the cutting edge or edges of the blade so that it is applied immediately after hairs are severed.

In accordance with a further aspect of the invention, the razor is packaged in a container with the liquid and used as a single-use razor for shaving and/or medical purposes.

In accordance with still a further aspect of the invention, the liquid comprises a mixture which functions as a deodorant when applied as the underarms are shaved or as a deodorant applied without shaving.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

Figure 1:
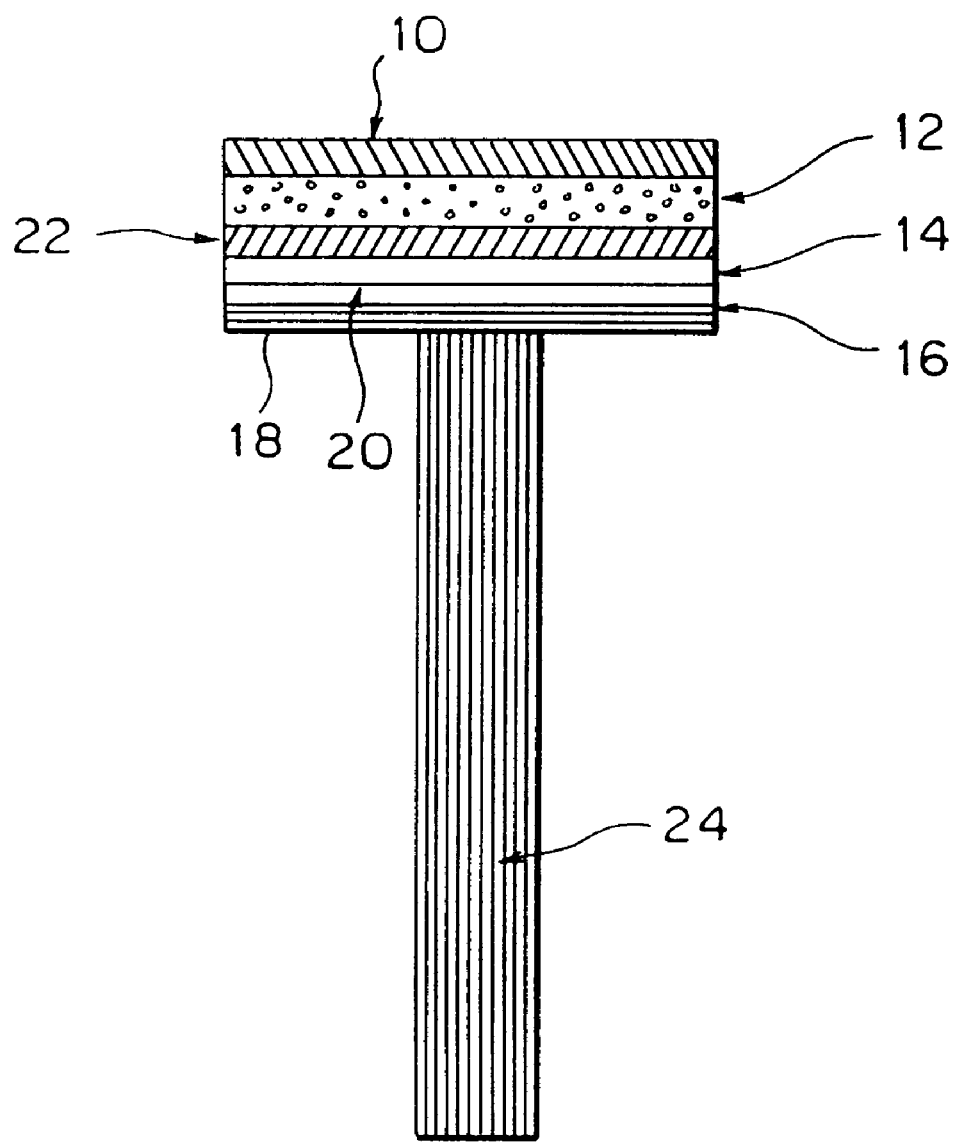
FIG. 1 is a front view of a razor including a strip of sponge material thereon.

Referring now to FIG. 1, there is shown a conventional razor 10 (also known in the art as a shaver) modified to include a liquid retainer in the form of a sponge strip 12 disposed behind a pair of blades 14 and 16 so as to trail the cutting edges 18 and 20 of the blades as the blades sever whiskers, leg hair or underarm hair. The sponge 12 and blades 14 and 16 are mounted on a shaving head 22 which is connected to a shaving handle 24.

While the sponge strip 12 is preferred, it is an improvement to a basic concept which will now be described.

Figure 2:
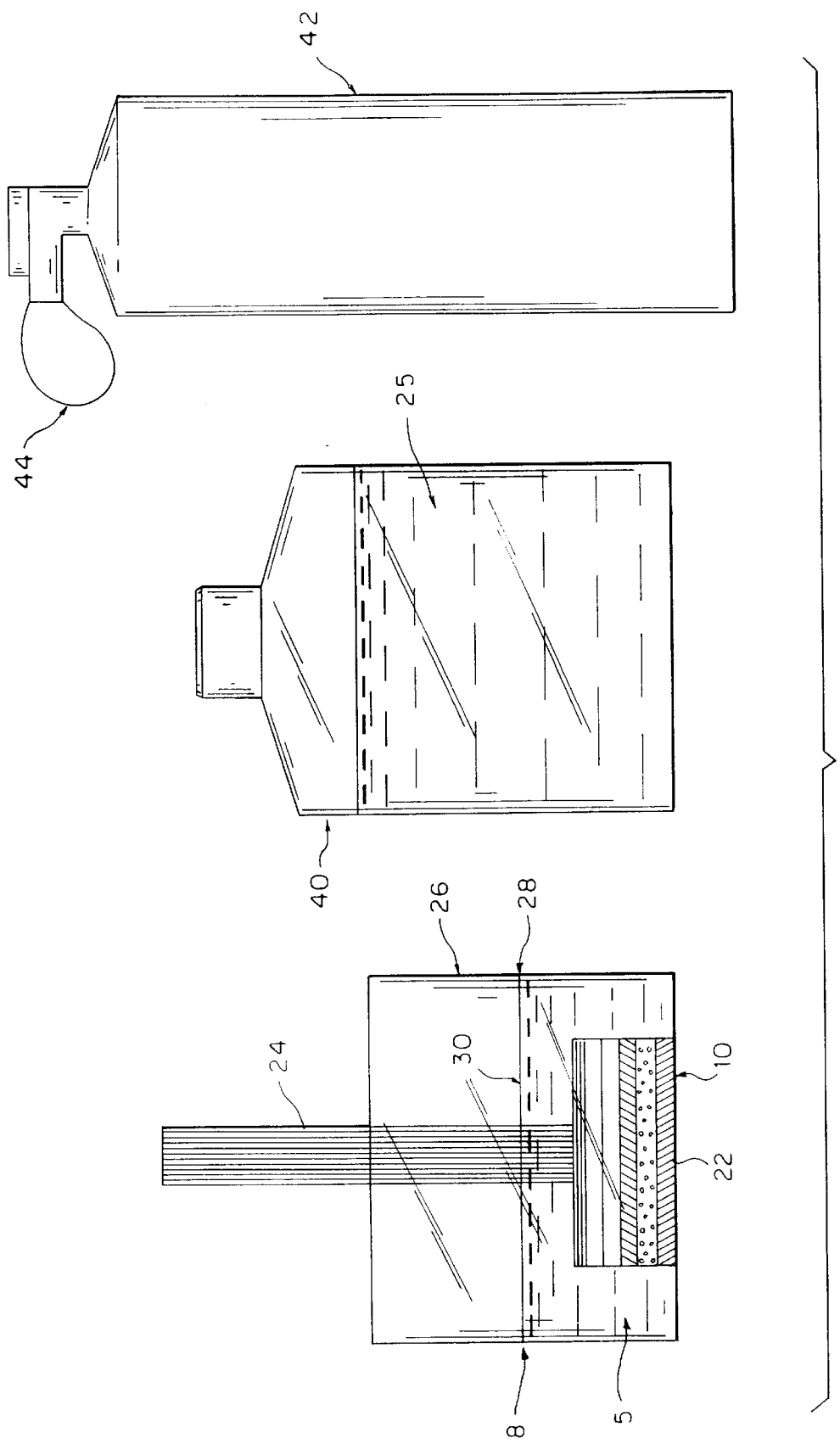
FIG. 2 is a view of the razor of FIG. 1 soaking in a quantity of liquid between shaves, with a bottle of the liquid as well as shaving cream or lather also being illustrated.

Referring now to FIG. 2, after shaving, preferably after each shave, the head 22 of the razor 20 is immersed in a bath 25 within a container 26, typically overnight. The bath 25 is filled to a level 28 in the container sufficient to cover the head 22. The bath 25 has a surface 30 which is exposed to the atmosphere to allow the liquid comprising the bath to slowly evaporate cooling the bath.

The liquid in the bath 25 is replaced from a bottle 40 periodically after the bath has become cloudy with shaving debris which includes shaved whiskers and used lather from a source of lather 42 which, in accordance with the present invention, can be an aerosol-type lather or any other type of lather utilized for shaving, including shaving gel. Typically, the bath can be changed once every two weeks or perhaps once a week.

The liquid comprising the bath 25 is preferably a solution of witch hazel and alcohol which is an astringent as well as an evaporative liquid so that when the razor 22 is removed from the bath 25, liquid remaining on the blades 14 and 16 begins evaporating and cools the blade(s). This is in addition to evaporation from the surface 30 of the liquid bath 25 which keeps the bath at a relatively low temperature with respect to room temperature. The act of moving the razor through the atmosphere to one's beard further cools the razor. By cooling the blade(s) of the razor, the metal comprising the edges 18 and 20 is contracted and tends to remain sharp. In addition, the edges 18 and 20 are substantially free of shaving debris such as whiskers and spent lather which may have substantially corroded the edges 18 and 20 overnight, the debris having been displaced while soaking the razor head 22 in the bath.

In use, the person shaving applies lather 44 to his face and then grasps the razor 10 by the handle 24 in a conventional manner to remove the razor from the bath 25. While the razor is still wet with the liquid comprising the bath 25, the shaver shaves his face. It may be necessary or desirable to rinse the spent lather from the blades 14 and 16 up to several times during a shave, but it is not always necessary to rinse the razor and reapply the liquid if the shaver was a light beard. The resulting shave is rapid and comfortable. If there happen to be cuts, the witch hazel alleviates pain as well as constricting the cuts to rapidly interrupt bleeding. Moreover, the astringent is applied simultaneously as whiskers are cut which appears to have some immediate effect on the whiskers and skin so as to provide a rapid and smooth shave.

The sponge strip 12 dispenses a generous quantity of the liquid comprising the bath 25 immediately after the edges 18 and 20 have severed whiskers or hair. This results in a very soothing shave.

After the shave has been completed, the shaver rinses the shaving head 22 in the usual way with tap water and places the shaving head 22 in the bath 25 as is shown in FIG. 2. The bath 25 removes remaining whisker and hair particles, used lather, tap water and tap water contaminants from the blades 14 and 16. More specifically, the bath 25 displaces these materials from the edges 18 and 20 of the blades. Later in the day or the next morning, whenever the subsequent shave occurs, the razor 10 is removed from the bath 25 and used to shave again in the aforedescribed manner. This process has been repeated as many as forty-two times without changing the head of a razor 10. Typically, the shaver head is immersed for the first time in the liquid for at least one hour or so, the precise time not being critical. Normally, it is immersed overnight between shaves for at least for 1–8 hours, e.g., 2, 4, 6, 8 hours, etc., the precise time not being critical.

It has been found that the useful life time of the cutting edges 18 and 20 of the blades 14 and 16 is extended substantially using the aforementioned process. For example, Trac II® (without the sponge strip 12) razor heads have been used for six weeks without changing the razor heads. This occurred when using water which normally requires that the heads 22 be replaced every 4–6 days. Since shaving heads 22, such as Gillette Trac II®s, are relatively expensive, utilizing the system and method of the present invention results in considerable cost savings in addition to very smooth, comfortable, quick shaves.

It has been found that if the liquid comprising the bath 25 is sprayed or otherwise applied on a woman's legs, the liquid will adhere to her legs instead of sliding off as is the case with conventional lather. This is especially the case if the liquid is applied while her legs are wet from bathing or showering. The resulting shave is smooth and substantially free of cuts and irritation. In addition, her legs are left smooth and fragrant.

Figure 3:
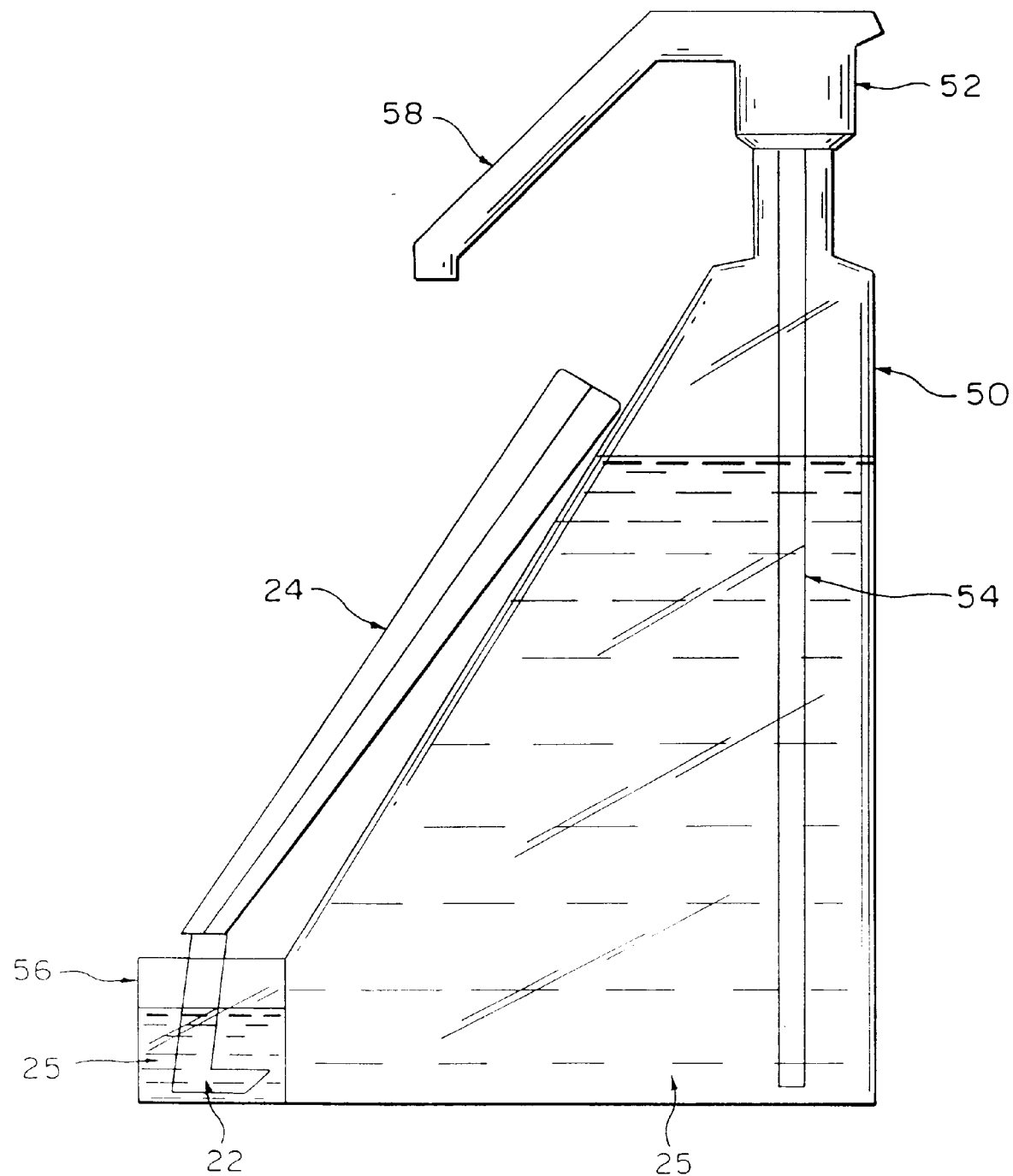
FIG. 3 is a side view, partially in section, showing an apparatus for facilitating employment of the shaving system in practicing the method.

Referring now to FIG. 3, there is shown a container 50 initially filled with the bath 25. The container 50 includes a conventional pump 52 with a dip tube 54 and an integral or unitary cup 56 which is aligned with a spout 58 connected to the pump. In use, the cut 56 is filled from the spout 58 to provide the bath 25 and the razor head 22 is soaked in the liquid bath with the handle 24 of the razor extending upwardly.

Figure 4:
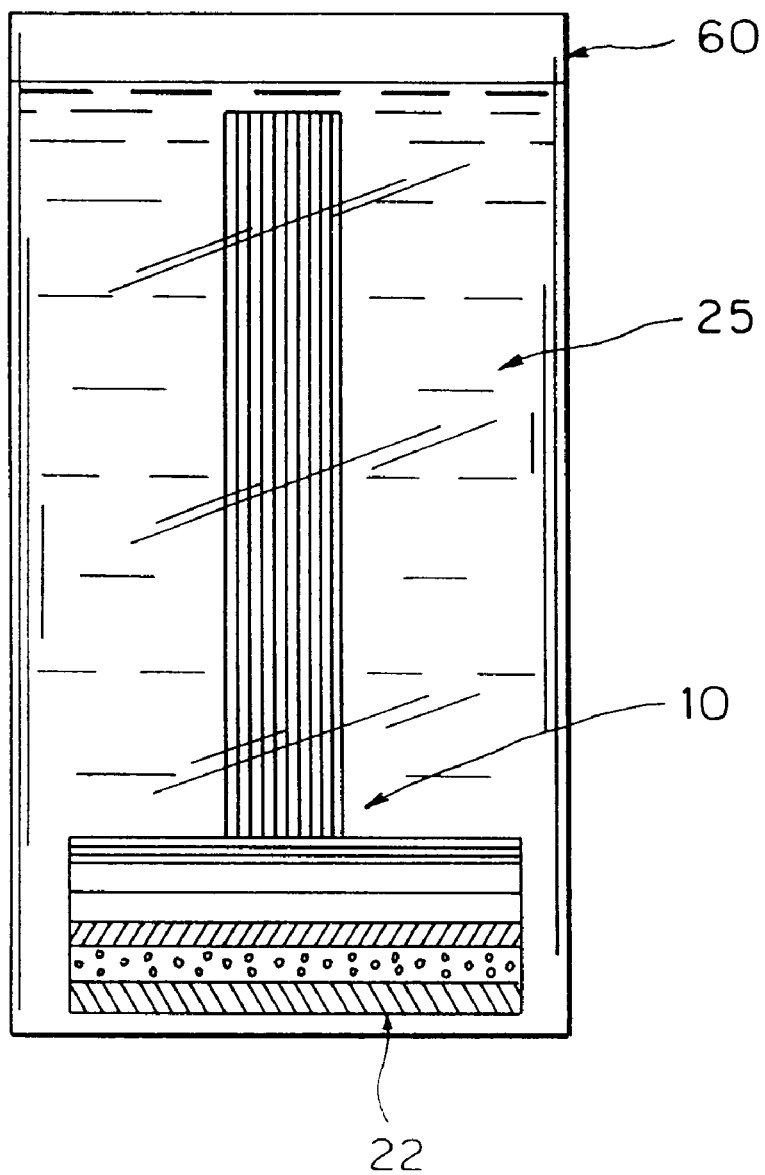
FIG. 4 is a front view of an assemblage configured for medical use including a pouch for containing a shaving bath compiled according to the present invention in combination with a disposable razor.

Referring now to FIG. 4, there is shown a container such as a flexible pouch 60 containing the razor bath 25 in which a disposable razor 10 is sealed. The arrangement of FIG. 4 is useful for single-use medical or other purposes. After the razor 10 is used once, both the razor 10 and pouch 60 are disposed of. Instead of a flexible pouch, a rigid container may be used to facilitate repeated dipping of the blades 14 and 16 on the razor.

Without intending to limit this invention in any way or to be bound by theory, it is believed that the extended life of the cutting edges 16 and 18 of blades 14 and 16 when submerged in a witch hazel bath 25 after each shave is attributable to the anti-oxidant properties of witch hazel as is set forth in U.S. Pat. No. 4,741,915 issued May 3, 1988 and incorporated herein by reference. By removing dissolved oxygen from proximity with the edges 16 and 18 of the blades 14 and 16 it is theorized that, degradation of the blade edges 16 and 18 is substantially reduced. Since the witch hazel is a solution containing about 14% alcohol, the bath 25 remains sterile and cool. Moreover, the alcohol denatures and dissolves substances in the bath 25 which may attach to or corrode the blade edges 18 and 20.

The active ingredient in witch hazel is "Hamameli tannin" from the bark of Hamamelis viginica, the sugar of which is hamamelose or α-oxymethyl-ribose. It is further believed that Hamameli tannin not only provides an astringent action, but also interacts with the metal of the blade edges 18 and 20 to preserve their sharpness. Thus, this invention also relates to a method of extending the lifetime or sharpness of a metal cutting edge comprising immersing the cutting edge in a liquid comprising witch hazel for a time effective to extend said sharpness lifetime. Such cutting edges include not only razors but also pocket knives, kitchen knives, etc. The time of immersion and witch hazel content of the solution is in accordance wit this specification.

While the bath 25 may be "off-the-shelf" witch hazel, such as E. E. Dickinson's® witch hazel, T. N. Dickinson's® witch hazel or Thayers® witch hazel composition. It has been found that adding additional materials to the witch hazel as described as follows improves the shave. Moreover, Thayers'® witch hazel, which has additional ingredients is preferred. Such Thayers® witch hazel includes the following ingredients:

1. Witch hazel extract
2. Aloe vera
3. Essential oils in water
4. Specially denatured alcohol
5. Emulsifiers in the form of a corn derivative which dissolves essential oils Thayers'® witch hazel is available from Henry Thayer and Company, P.O. Box 6207, Lincoln, Mass. 01773-6207.

The principal component in the astringent liquid to be used in this invention is "witch hazel extract," a well known composition of mater derived conventionally from the mentioned bark. Suitable for such extract compositions are those which are used in the commercially available "witch hazel" compositions mentioned above, for example. Methods of making such extract preparations are very conventional and have been carried out for many decades. "Witch hazel," as opposed to "witch hazel extract," contains in addition to the extract about 14% alcohol, typically isopropyl alcohol. (In the examples below, witch hazel is employed, not the extract.)

The precise amount of witch hazel extract employed in the liquid of this invention is not particularly critical as long as sufficient extract is contained to achieve the effects of the invention. Typically, the relative amount used in commercial witch hazel formulations will be used. Such extract contents, however, can be increased and even decreased, e.g., the 5, 10, etc. percent.; Whereas isopropyl alcohol is preferred, e.g., preferring in a content of about 14%, but also in larger a smaller amount, e.g., 10–20%, or other amounts, other alcohols can be used, e.g.,ethanol, butyryl, isopropyl alcohol,k etc., in equivalent amounts. Other ingredients can also be used which evaporate at room temperature, and/or which are anticeptic, and/or which are astringents, etc. in routinely determinable amounts in view of this disclosure. Also useful are wetting agents (e.g., OSP 3063907 and others), astringents as mentioned about, lubricants (e.g., aloe vera, glycerine, lanoline, etc), anti-dry skin agents (e.g., NAPCA and those found in hand and body lotions), lotions, fragrances, flavorings, etc. The amounts used are not critical, e.g., typically amounts from 1–10% of each can be used, both greater and lesser amounts being employable also. Suitable such ingredients are conventional and may be found, e.g., in Remington's Practice of Pharmacy, Martin and Cook, 1956, The Mack Publishing Co., or U.S. Pharmacopeia.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all parts and percentages are by volume.

EXAMPLE 1

75% Witch Hazel

20% Sea Breeze ® Distr. By: Bristol-Myers Squibb Co.

5% Aloe Vera

EXAMPLE 2

100% Witch Hazel (E. E. Dickenson', T. N. Dickensons or Thayers®, each of which contains about 86% witch hazel extract and about 14% alcohol)

EXAMPLE 3

About 70% Witch Hazel (14% alcohol)

About 10% Rosewater with Glycerin

About 10% available from Twinlab®, Michelle Lazar Cosmetics, San Bernadino, Calif.

About 5% Aloe Vera Juice

About 5% Spearmint Extract

Example 3 provides a very fragrant mixture for a razor bath 25 that will even make the surrounding environment smell fresh.

EXAMPLE 4

About 75% Witch Hazel

About 10% Aloe Vera Juice

About 5% Rose Water

About 2.5% Glycerin

About 2% Rubbing Alcohol

About 0.5% Spearmint Extract

About 5% available from Twinlab®, Michelle Lazar Cosmetics, San Bernadino, Calif.

Example 4 provides a desired mixture for the liquid bath 25 with an extra smooth feel, better suited for body shaving in which in addition to using the razor 10 soaked in the liquid bath, the mixture is sprayed on one user's legs and/or underarms after showering and immediately before shaving. This mixture does not slide off west legs and underarms as in the case with using just lather. No lather is necessary with this mixture.

EXAMPLE 5

About 50% Witch Hazel (14% alcohol)

About 10% Rose Water

About 10% Aloe Vera

About 5% Glycerin

About 10% NAPCA

About 2.5% Spearmint Extract

About 5% Rubbing Alcohol

About 5% Lemon Juice

About 0.5% Vitamin E

About 2.0% White Distilled Vinegar

Example 5 provides a desired mixture for extra cooling sensation and greater skin cleansing and healing. In addition, the solution or mixture of Example 5 works as a deodorant which does not utilize aluminum The preceding examples can be repeated with similar success by substituting the generically or specifically described reactants and/or operating conditions of this invention for those used in the preceding examples.

The entire disclosure of all patent applications, patents and publications and products cited herein are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A shaving kit comprising:
    a shaving razor having at least one blade;
    a solution of witch hazel; and
    a soaking container receiving the solution of witch hazel for storing the razor with the blade thereof in the witch hazel after each shave to prolong the life of the blade and for dipping the razor in the solution of witch hazel during shaving to provide a smooth comfortable shave with minimal nicks and cuts.

2. The kit of claim 1, wherein shaving lather is included in the kit for application to the shaver's face or body prior to shaving.

3. The kit of claim 1, wherein the witch hazel solution further comprises a lubricant oil.

4. The kit of claim 1, wherein the razor further includes a liquid retainer thereon disposed proximate the blade for retaining a quantity of the witch hazel solution on the razor during shaving.

5. The kit of claim 1 wherein the witch hazel and solution is less than 100% of the liquid bath with the remainder of the liquid bath including a lubricant.

6. The kit of claim 5 wherein the lubricant comprises aloe vera.

7. The kit of claim 6 wherein the lubricant further comprises glycerin.

8. The kit of claim 5 wherein the witch hazel solution further comprises NAPCA.

9. The kit of claim 8 further including a spray bottle containing the witch hazel solution wherein the person using the kit sprays the witch hazel solution on the area to be shaved before shaving with a razor.

10. The kit of claim 1, wherein the witch hazel solution comprises the following components:
    about 70% witch hazel (14% alcohol)
    about 10% rose water with glycerin
    about 10% NAPCA
    about 5% aloe vera juice
    about 5% spearmint extract.

11. The kit of claim 1, wherein the witch hazel solution comprises the following components:

about 75% witch hazel (14% alcohol)
about 10% aloe vera juice
about 5% rose water
about 2.5% glycerin
about 2% rubbing alcohol
about 0.5% spearmint extract
about 5% NAPCA.

12. The kit of claim 1, wherein the witch hazel solution comprises the following components:
about 50% witch hazel (14% alcohol)
about 10% rose water
about 10% aloe vera
about 5% glycerin
about 10% NAPCA
about 2.5% spearmint extract
about 5% rubbing alcohol
about 5% lemon juice
about 0.5% vitamin E
about 2.0% white distilled vinegar.

13. The kit of claim 1 further including a dispenser for the witch hazel solution with a pump integral therewith for pumping the witch hazel solution into a cup connected to the reservoir to provide a bath, wherein the cup has a width sufficient to receive the head of the razor so that the blade of the razor is immersed in the bath.

14. The kit of claim 12 wherein the liquid is also used as an underarm deodorant.

15. A kit for shaving, useful for medical purposes, comprising a container with a solution of witch hazel extract and alcohol therein and a disposable razor immersed in the solution, the container being initially sealed.

* * * * *